United States Patent
Russell

(10) Patent No.: US 6,863,076 B2
(45) Date of Patent: Mar. 8, 2005

(54) FOIL FOR USE IN HAIR COLORING, AND METHOD OF USE

(75) Inventor: Marsha A. Russell, Salem, MA (US)

(73) Assignee: PWAI, LLC, Salem, MA (US)

( * ) Notice: Subject to any disclaimer, the term of this patent is extended or adjusted under 35 U.S.C. 154(b) by 116 days.

(21) Appl. No.: 10/329,815

(22) Filed: Dec. 23, 2002

(65) Prior Publication Data

US 2004/0118424 A1 Jun. 24, 2004

(51) Int. Cl.⁷ .............................. A45D 2/00; A61K 7/13
(52) U.S. Cl. ...................................... 132/222; 132/208
(58) Field of Search ................................ 132/222, 270, 132/221, 207

(56) References Cited

U.S. PATENT DOCUMENTS

| | | | |
|---|---|---|---|
| 757,204 A | | 4/1904 | Keonig |
| 1,719,555 A | * | 7/1929 | Lewis et al. ................. 132/222 |
| 2,475,998 A | | 7/1949 | Soergel |
| 3,304,945 A | | 2/1967 | Anderson |
| 4,196,741 A | | 4/1980 | Minghenelli |
| 4,403,622 A | * | 9/1983 | Stahl ........................... 132/243 |
| 4,552,159 A | | 11/1985 | Fabbri et al. |
| 4,655,377 A | | 4/1987 | Orangeo, Jr. et al. |
| 4,672,983 A | * | 6/1987 | Nath et al. ................... 132/208 |
| 5,007,443 A | * | 4/1991 | Fulgoni ........................ 132/270 |
| 5,058,609 A | | 10/1991 | Sandoz et al. |
| 5,156,172 A | | 10/1992 | Tancredi |
| 5,287,864 A | | 2/1994 | Gallo |
| 5,335,679 A | | 8/1994 | Baxter |
| 5,538,021 A | * | 7/1996 | Kim ............................ 132/222 |
| 5,549,126 A | | 8/1996 | Green |
| 5,799,669 A | | 9/1998 | Briggs |
| 5,824,384 A | * | 10/1998 | Hickox ........................ 428/61 |
| 5,860,431 A | | 1/1999 | Abercrombie et al. |
| 5,931,168 A | | 8/1999 | Abercrombie et al. |

OTHER PUBLICATIONS

PCT International Search Report dated Aug. 17, 2004 of International Application No. PCT/US03/39997 filed Dec. 17, 2003.

* cited by examiner

Primary Examiner—John J. Wilson
Assistant Examiner—Robyn Doan
(74) Attorney, Agent, or Firm—Maine & Asmus

(57) ABSTRACT

A foil for use in hair coloring is made of a substantially rectangular sheet of material. The upper edge of the foil is pinked, forming a zig-zag pattern. The upper surface of the foil contains a hair restraint in proximity to the foil's upper edge, formed of an elongated, rectangular strip of loop material which adheres to the hair. The lower surface of the foil contains a similar elongated rectangular strip of loop material, providing an attachment anchor, which adheres to the scalp of the subject without the stylist having to hold the foil during the entire coloring process. After the foil has been attached to the subject's hair in proximity to a part, hair strands are woven from under the foil, over the upper edge, and held in place by the hair restraint. Coloring is then applied, and the foil folded in half, retaining the hair within the folded foil.

13 Claims, 12 Drawing Sheets

FOIL FOR USE IN HAIR COLORING, AND METHOD OF USE

FIELD OF THE INVENTION

The present invention is a method for frosting and/or coloring hair using a novel foil and a method of its use

BACKGROUND OF THE INVENTION

The present invention is directed to the technology of the coloring of hair, in its various forms, including, but not limited to, highlighting and frosting. These techniques are used to change the color of a person's hair. In particular, frosting or highlighting involve the coloring of selected strands of hair, while leaving other strands their natural color, or another color. Such coloring techniques are by nature time consuming and expensive.

A number of different methods have been used to accomplish frosting in the prior art. One of the most common involves the use of a foil. Using a small rectangular sheet of chemical-impervious material, strands of hair to be colored are separated from the subject's hair and placed on the foil. Coloring chemicals are then applied to the hair, using a brush, foam, or sponge. The foil is then folded about the colored strands. The process is repeated for each area of the hair to be frosted. Eventually, dozens or more separate foils cover the subject's head, and these are left in place while the coloring agents do their work. Finally, the foils are removed and disposed of.

The foil method is inexpensive as far as the materials are concerned, but extremely time consuming and therefore expensive because of the labor costs involved. The foils are typically made of a coated metal foil material. They must be cut to the desired size for each area of the subject's head to be frosted. More importantly, the stylist must use one hand to maintain the foil in place while the hair strands to be colored are selected, typically using the "pick" at the end of a comb. After the strands are selected, the hair stylist, still holding the foil in one hand, applies the coloring agent with the other. The process is awkward, and the stylist must be sure to keep all the materials required within easy reach. Only after the foil has been folded can the foil be released, since at this point the coloring agents act as an adhesive, holding the foil in place by adhering to the foil and the hair within.

Even when the stylist is practiced and careful, the foil may move about during the application of the coloring agent, resulting in the coloring of other, undesired portions of hair. In addition, there exists the danger of seepage of the coloring agent from the foil, with the same result.

Furthermore, because of the time involved in this process, the stylist often has difficulty in maintaining the coloring agents at the desired time in each foil to maintain a consistent coloring throughout the scalp. There remains a persistent problem of coloring too much or too little of the hair, due, in part, to timing problems relating to the amount of time the coloring agent is on the hair.

Other methods of frosting have been used in order to attempt to circumvent the problems of the foil method. These include covering the subject's hair with a cap having a number of holes formed within, and pulling strands of hair through the holes using a hook or other suitable device. A coloring agent can then be applied to the strands extending through the cap. However, this method has a number of problems associated, not the least of which that it is painful for many subjects.

The present foil and its method of use substantially solve the problems of the prior art. The advantages of the foil method are maintained, including the simplicity and low cost the foils themselves. The current invention provides a foil which clings to the hair even before the strands are selected for coloring, so that the stylist is free to move about during the application. The foil of the current invention also maintains the selected strands in place before the foil is folded, so that constant adjustment of the strands, as in the prior art, is not required. The result is that the coloring process using the foils of the present invention proceeds at a fraction of the time required by method using the prior art foils.

The present invention also allows the stylist to use foils of almost any width desired, even facilitating the frosting of half a head of hair with a single foil. Even very short hair, previously impossible to color using the prior art, can be easily colored using the current invention.

Because of the decreased time of the application of color using the present method, timing considerations are greatly reduced. Use of transparent windows in the foils, or making the foils out of transparent material, further relieves the problem of inconsistency in the color from one foil to the next.

SUMMARY OF THE INVENTION

It is an object of the present invention to provide a method for the frosting or coloring of hair which will simplify the process and reduce the time required in its application.

It is a further object of the present invention to provide an improved foil for hair coloring which will accelerate and simply the process.

In accordance with a first aspect of the invention a foil for use in hair coloring technology includes a sheet of rectangular material having a top edge, an attachment anchor having an elongated, substantially linear section of hair-adherent material attached to the lower surface of the foil substantially parallel to the top edge, and in proximity to it.

In accordance with a second aspect of the invention the hair-adherent material is loop fastener material.

In accordance with a third aspect of the invention the attachment anchor is substantially rectangular, having a first edge in proximity to the top edge.

In accordance with a fourth aspect of the invention the top edge is pinked the attachment anchor also has a pinked edge disposed in proximity to the pinked edge of the foil.

In accordance with a fifth aspect of the invention reinforcing material is attached to reinforce the pinked edge of the foil.

In accordance with a sixth aspect of the invention the foil also contains a hair positioning restraint formed from a substantially linear section of hair-adherent attached to the upper surface of the foil with its long axis substantially parallel to the top edge of the foil, and in proximity to it.

In accordance with a seventh aspect of the invention the long axis of the hair positioning restraint is about one-quarter inch from the top edge of the foil.

In accordance with an eighth aspect of the invention the lower surface of the sheet is coated with a moisture barrier, and the upper surface further is made of a slightly moisture absorbent material.

In accordance with a ninth aspect of the invention the user attaches the foil to the hair in proximity to a part the attachment anchor to hold the foil in place on the subject's scalp by placing the top edge of the foil near the bottom of a part to retain the foil securely in position with the top edge close to the scalp.

In accordance with a tenth aspect of the invention the stylist uses a pick attached to a comb to draw strands of hair from under the foil through the attachment anchor on the underside of the foil.

In accordance with an eleventh aspect of the invention, the stylist presses the strands of hair against the positioning restraint to hold them down in a separated pattern.

In accordance with a twelfth aspect of the invention, the foil contains one or more transparent windows to allow the stylist to view the progress of the coloring process.

In accordance with a thirteenth aspect of the invention the foil is made of a transparent material.

In accordance with a final aspect of the invention the stylist pushes up on the positioning restraint to realign it in its original position.

BRIEF DESCRIPTION OF DRAWINGS

These, and further features of the invention, may be better understood with reference to the accompanying specification and drawings depicting the preferred embodiment, in which:

FIG. 4b depicts an elevation view of the embodiment FIG. 4a.

PREFERRED EMBODIMENTS

The invention is implemented in its preferred embodiment by use of a modified foil, so called because prior art articles of manufacture used in the current application have been called "foils", whether or not made of metallic foil.

In the prior art foils, strands of hair are "woven", that is to say, hairs in a certain region of the head are separated into those chosen to be colored, and others in proximity to the chosen hairs.

Figure 1A:
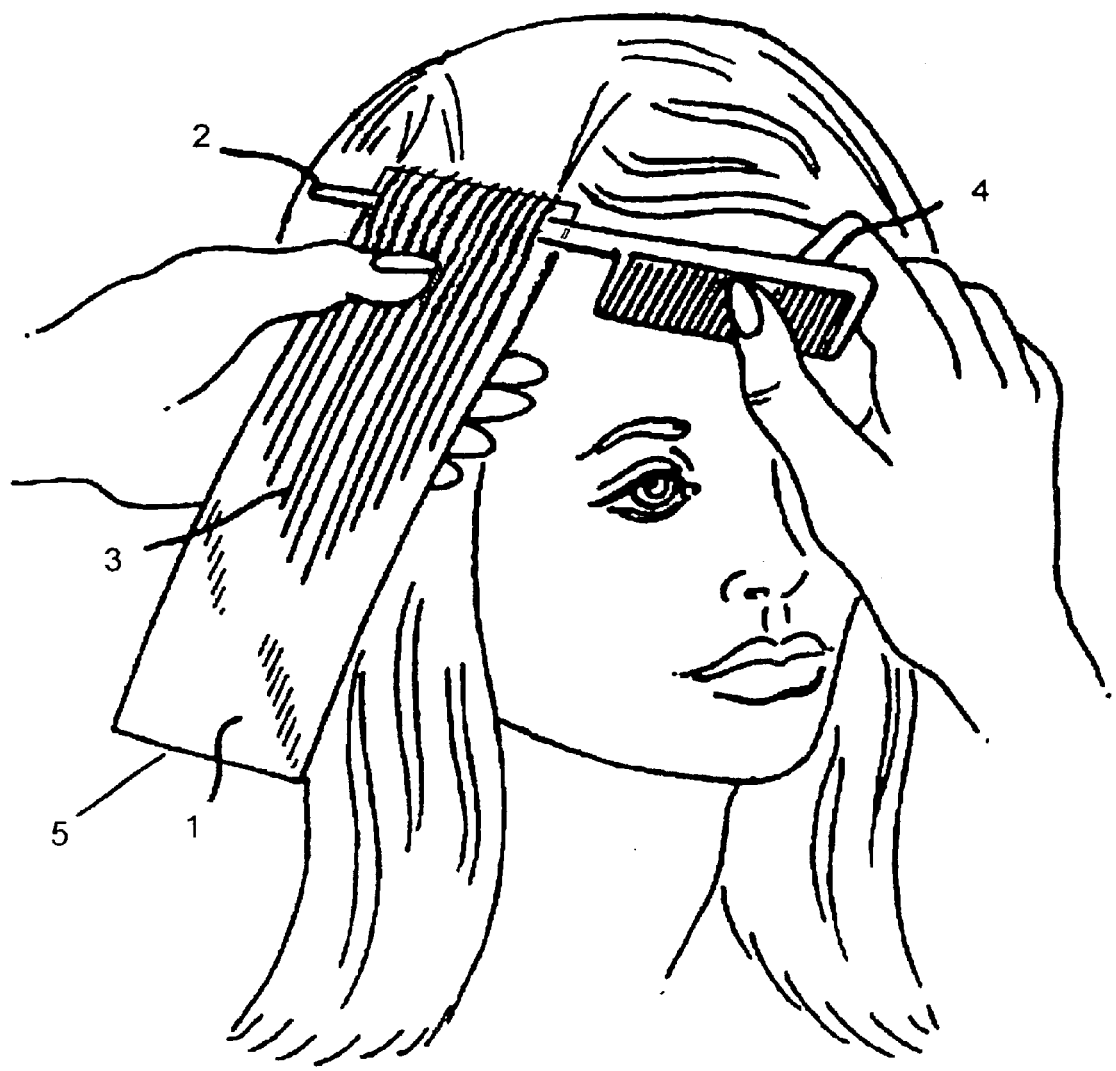
FIG. 1a depicts a first step in the use of a prior art foil.

As previously noted, one of major advantages of the present invention is that it clings to the head of the subject whose hair is being colored, without the stylist having to hold the foil in place prior to it being folded, after the coloring chemicals have been applied. Referring again to FIG. 1a, note that the stylist requires both hands to manipulate the prior art foil 1. In this figure, the left hand holds the foil, while the right uses the "pick" or "rat tail" 2 end of the comb 4 to "weave" the hair, placing strands 3 on the upper surface of the foil, to which color will be applied.

Figure 1B:
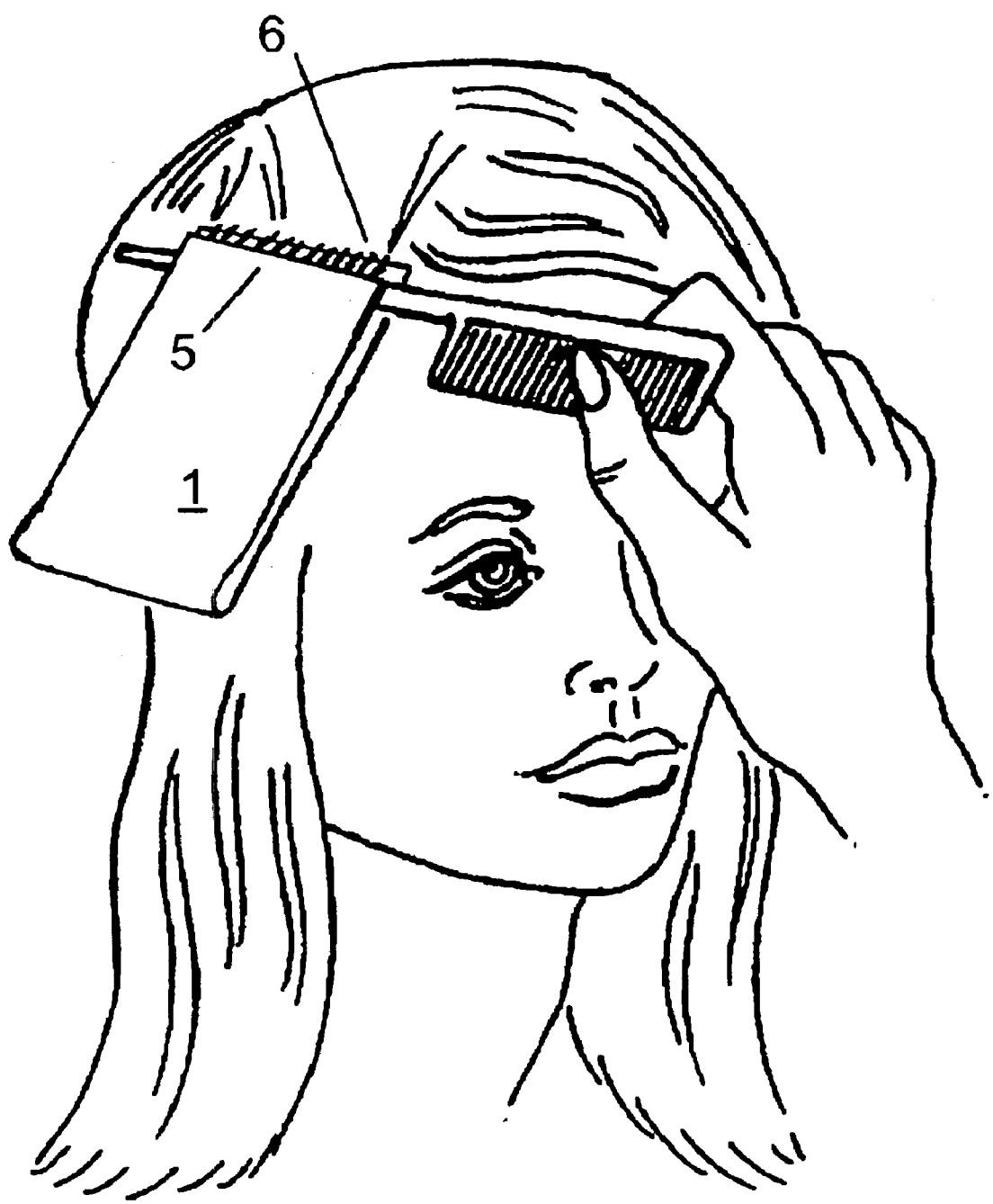
FIG. 1b depicts a second step in the use of a prior art foil.

Referring next to the second prior art drawing FIG. 1b, after application of the hair coloring chemicals to the woven strands 3, the foil 1 has been folded in half, so that the bottom edge 5 is now lying in proximity to the top edge 6. The stylist may now remove the comb, since, in the prior art, the folding of the foil after application of the coloring will usually provide adhesion of the foil 1 to the hair strands 3, holding them in place within the folded foil, and allowing the foil to remain on the head while the coloring takes effect.

The current invention provides a foil which will adhere to the hair, so that the stylist can first dispose the foil in position on the subject's head prior to the weaving, without having to hold the foil in place thereafter for support, since the foil contains means to hold the lower surface on the head prior to weaving.

Referring first to FIGS. 2a through 2c and 3, the modified foil of the current invention is a substantially rectangular sheet of thin material with the ability to conform to the contour of the head. The lower surface 44 of the sheet contains a moisture barrier, while the upper surface 30 is slightly moisture absorbent so as to retain the liquid or paste chemicals applied to the hair of the subject, thereby preventing runoff of the chemicals.

The basic foil is approximately three inches in width and six inches in length. The top edge of the sheet is has a "pinked", or zigzag tooth pattern 30, which creates channels to spread the hair strands to be colored, and to maintain them in place. The term "pinked" as used throughout this disclosure and the claims that follow is clearly understood in the industry to mean an edge cut with a notched or serrated pattern.

Figure 3:
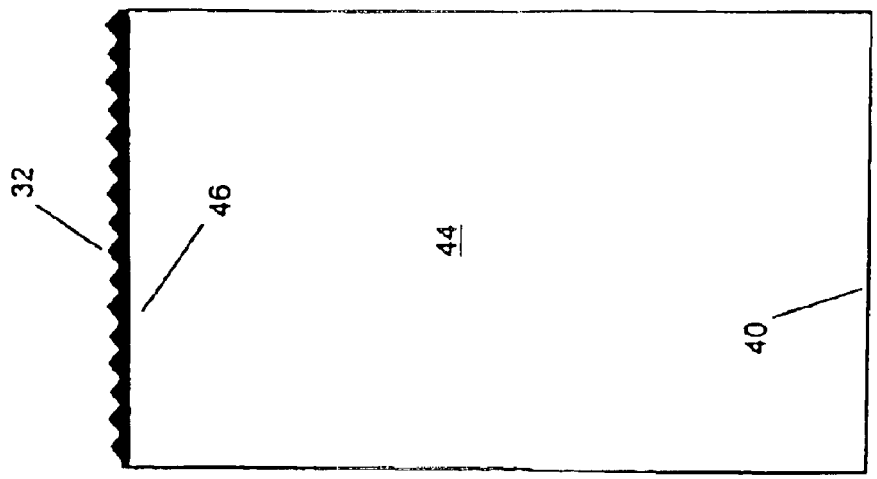
FIG. 3 depicts the lower side of the foil.

Referring now to FIG. 3, the top edge of the lower surface of the current foil contains an attachment anchor 46 which holds the foil close to the scalp by means of hooks, teeth, or other hair-grasping features of the material. Loop-material of the hook-and-loop variety, such as Velcro®. have been found to have ideal characteristics for this application, although many other materials have been found appropriate for this application. As seen in FIG. 3, the attachment anchor 46 is formed of an elongated, substantially rectangular piece of material, which is then pinked 30 to match the top edge 32 of the foil. The attachment anchor 46 further provides rigidity to the top edge of the foil, so that it does not curl or collapse. It is bonded to the foil by adhesive.

Figure 2C:
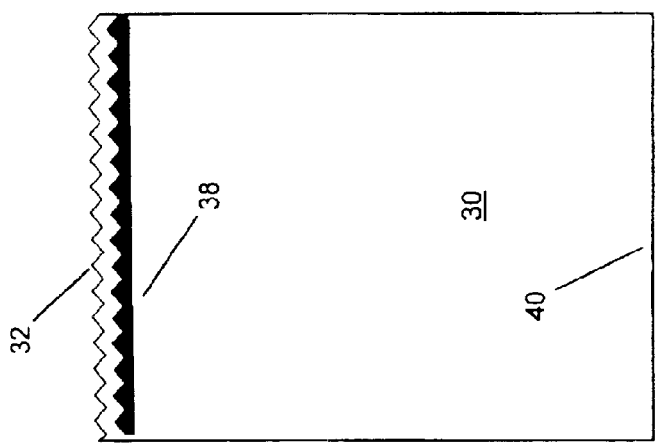
FIG. 2c depicts a third variation of the upper surface of the foil.
Figure 2B:
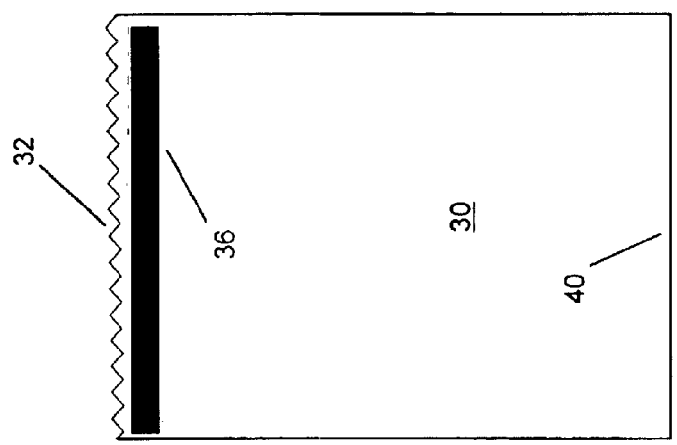
FIG. 2b depicts a second variation of the upper surface of the foil.
Figure 2A:
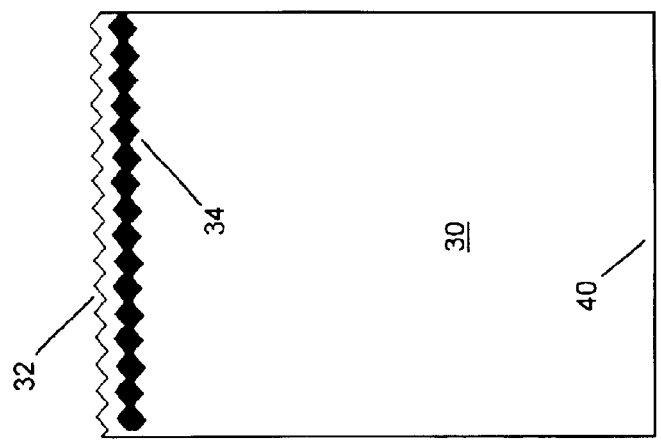
FIG. 2a depicts a first variation of the upper surface of the foil.

Referring again to FIGS. 2a through 2c, the upper surface of the foil also contains a hair positioning restraint, attached to the foil in proximity to the pinked edge, but displaced by about one-quarter inch from the pinked top edge. This positioning restraint is formed from an elongated, substantially rectangular piece of material, which is then pinked at its top 36. The positioning restraint may take one of several embodiments. In FIG. 2a, the positioning restraint 34 is pinked at the top and bottom edges, the top edge substantially matching the pattern of the pinked edge 32 of the foil. The embodiment of FIG. 2c is substantially rectangular, while that of FIG. 2c is pinked at the top edge, similar to the embodiment, but the bottom edge of the positioning restraint has a substantially rectangular configuration, as seen in the Figure.

The positioning restraint keeps the hairs to be colored in place on the upper surface of the foil, and further helps to attach the foil to the scalp of the subject. The positioning restraint is typically made of the same material as the attachment anchor, and a preferred material is Velcro® loop material, as previously mentioned. It is bonded to the foil by adhesive.

Figure 4B:
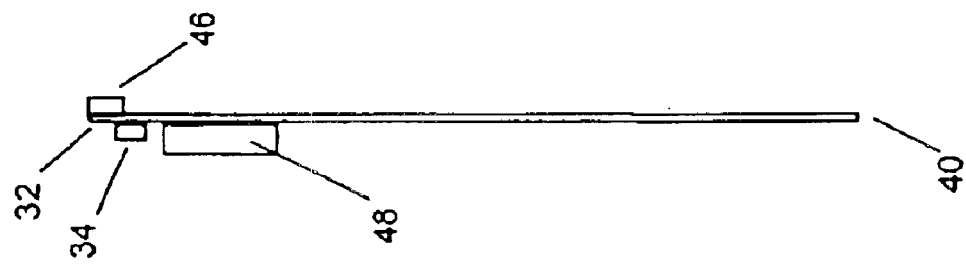
Figure 4A:
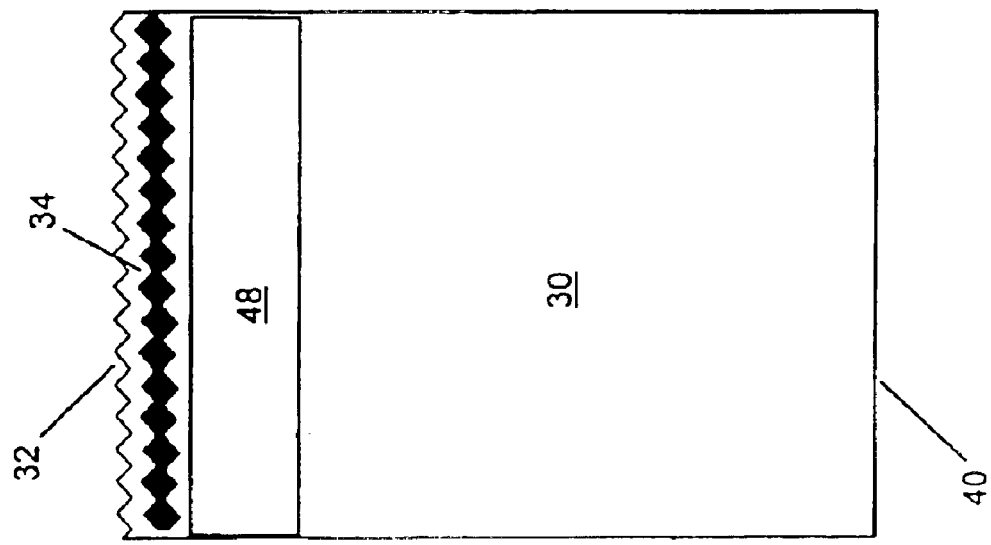
FIG. 4a depicts a plan view of an embodiment of the foil including a foam pad suitable for application of coloring chemicals for home use.

One further embodiment of the foil is depicted in FIGS. 4a and 4b, which contains a positioning restraint of the type shown in FIG. 2a, but can be of any of the types previously described. The embodiment of FIG. 4a contains a pad of a spongy foam material 48 with interconnecting cells, which is attached to the upper surface 30 of the foil by an adhesive. This foam pad serves as an application reservoir for the coloring chemicals to be applied to the hair. The foam pad may be made of any number of materials, including natural sponge, or synthetic sponge materials, such as cellulose. It is particularly applicable to versions of the foil provided for home use, while professional stylists will probably prefer to apply the chemicals themselves. In the embodiment of FIGS. 4a and 4b, the application reservoir will be loaded with the coloring chemicals in either paste form, or as a dried liquid, which must be moistened prior to use. A brush is used to transfer the chemicals from the sponge to the hair strands.

As seen in the top plan view of FIG. 4a, the application reservoir extends across the width of the foil, and is about an inch in width. In the elevation view of FIG. 4b, the application reservoir thickness is equal to, or slightly greater than that of the positioning restraint. It may not be significantly greater, or it will prevent the positioning restraint from holding the hair strands.

Figure 5:
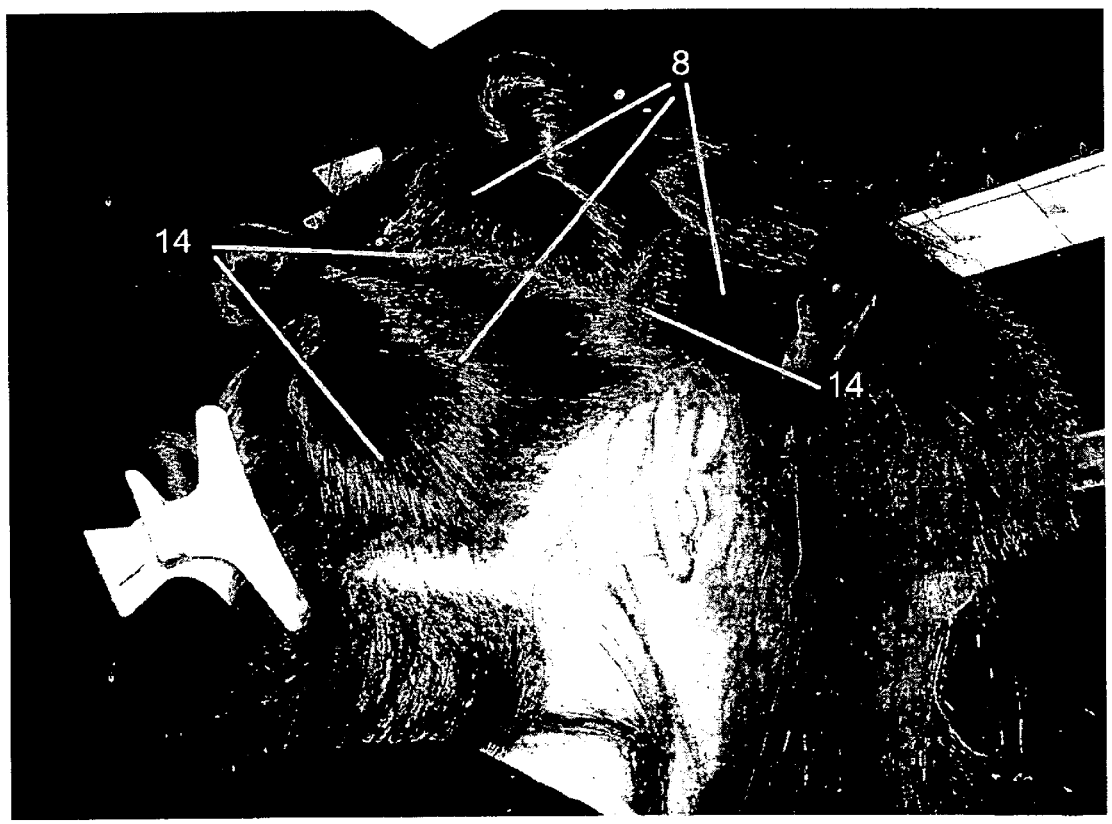
FIG. 5 depicts the separation of the hair of a subject into workable segments.

The process of coloring the hair with the foils of the current invention as described above starts by dividing the hair on the head into workable segments 8 separated by parts 14, as shown in FIG. 5. This simplifies the use of foils by moving hair out of the way that is not currently being worked on, and assisting in more uniform results thereby.

Figure 6:
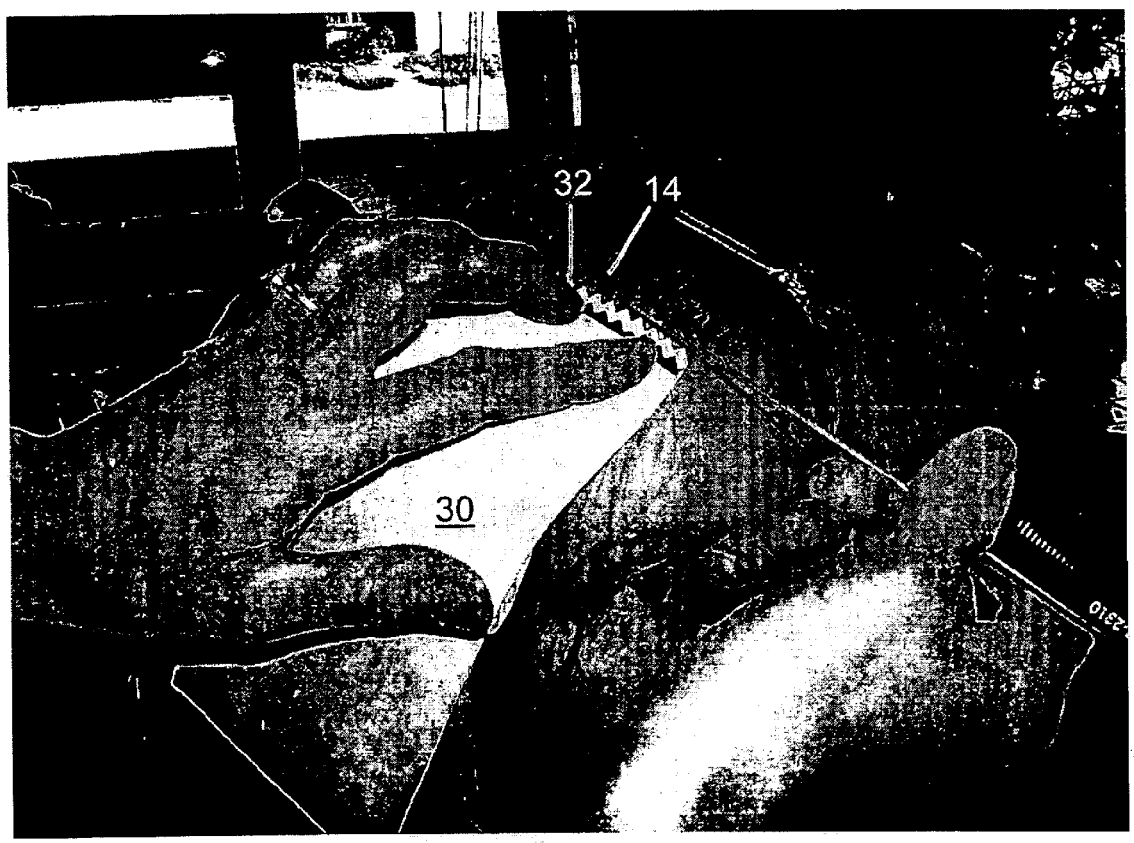
FIG. 6 depicts the attachment of the foil to the subject's hair.

Referring next to FIG. 6, the foil is next attached to the hair in proximity to a part line 14 using the attachment anchor material on the lower surface of the foil (not visible) to hold the foil in place on the subject's scalp. The zigzag design of the pinking on the top edge 32 of the foil is placed near the bottom of the part 14 to retain the foil securely in position with the top edge close to the scalp.

Figure 7:
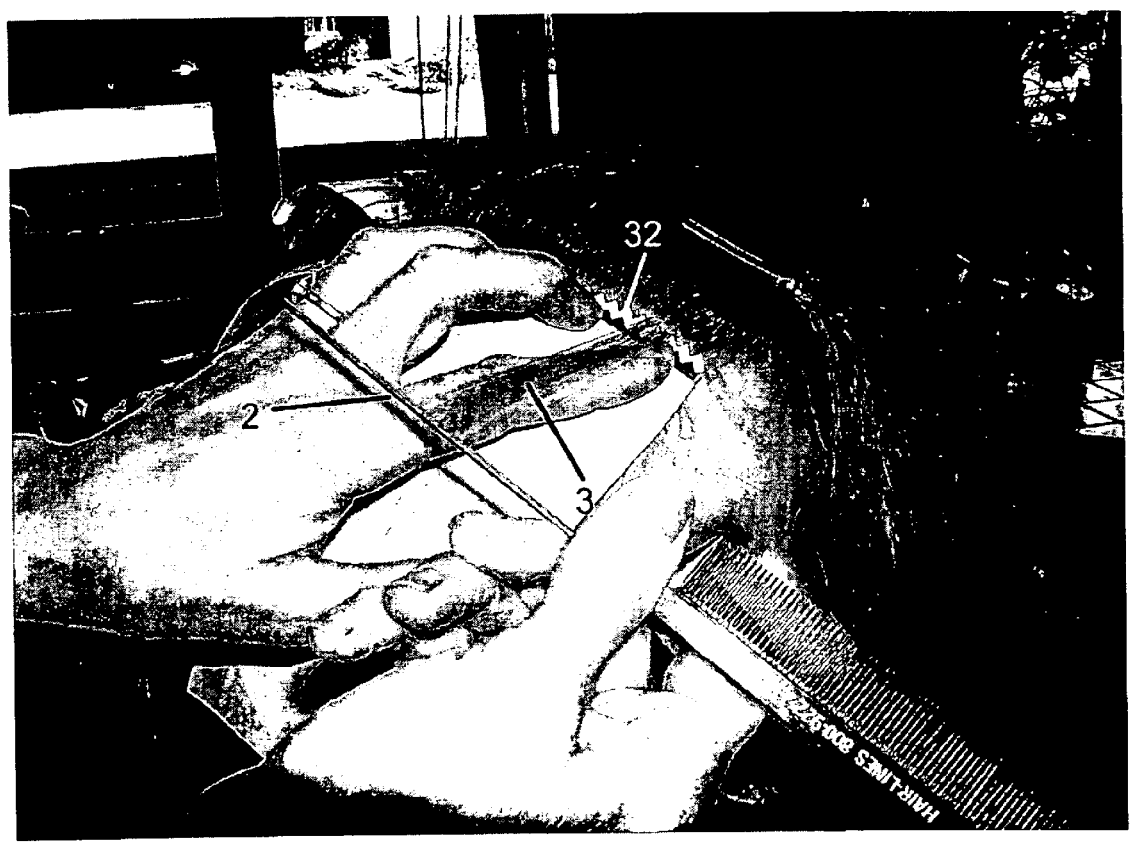
FIG. 7 depicts the weaving of hair from beneath the foil to the top of the foil.

Referring next to FIG. 7, the stylist, using a pick 2 attached to the comb, draws strands of hair 3 from under the foil, through the attachment anchor on the underside of the foil, and placed in the channels formed by the zigzag pattern of the pinking 32 on the top edge of the foil. Hair that is drawn from under the sheet will thus be "picked" along the entire top edge 32 of the foil, creating a uniform density of hair strands along the entire top edge of the foil. The density of hairs thus "picked" will be substantially less than the subjects normal hair density, so that only every n strands will be disposed at the top of the foil to be colored, where n may be any number desired.

The flexibility in choosing the density of strands to be colored, and to color very short lengths of air in the present invention allows for the creation of many patterns of color and designs which were not possible using the prior art.

Figure 8:
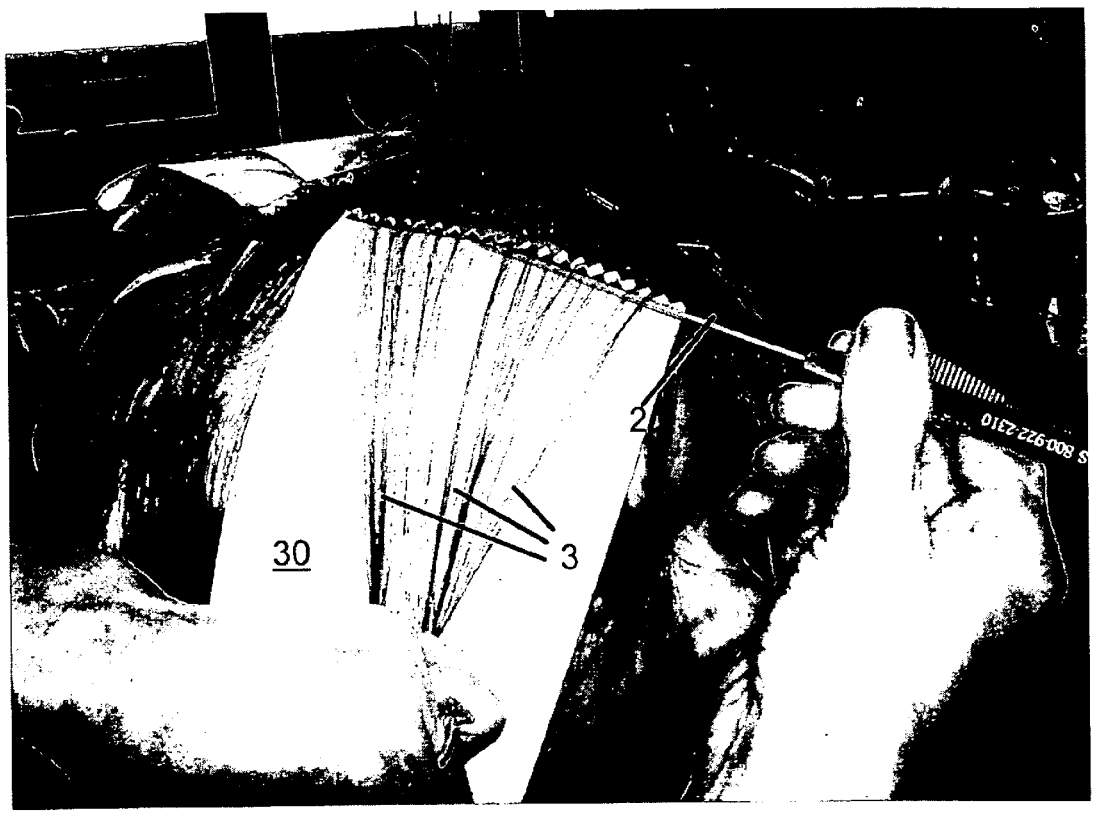
FIG. 8 depicts the attaching of the woven hair strands onto the hair restraint.

Referring next to FIG. 8, the stylist, pressing the hair 3 against the positioning restraint holds it down on the foil in a separated pattern. The pick 2 is now used to make a final adjustment of the foil by pushing up on the positioning restraint realigning it in the original position in the case that movement occurred through the process.

Figure 9:
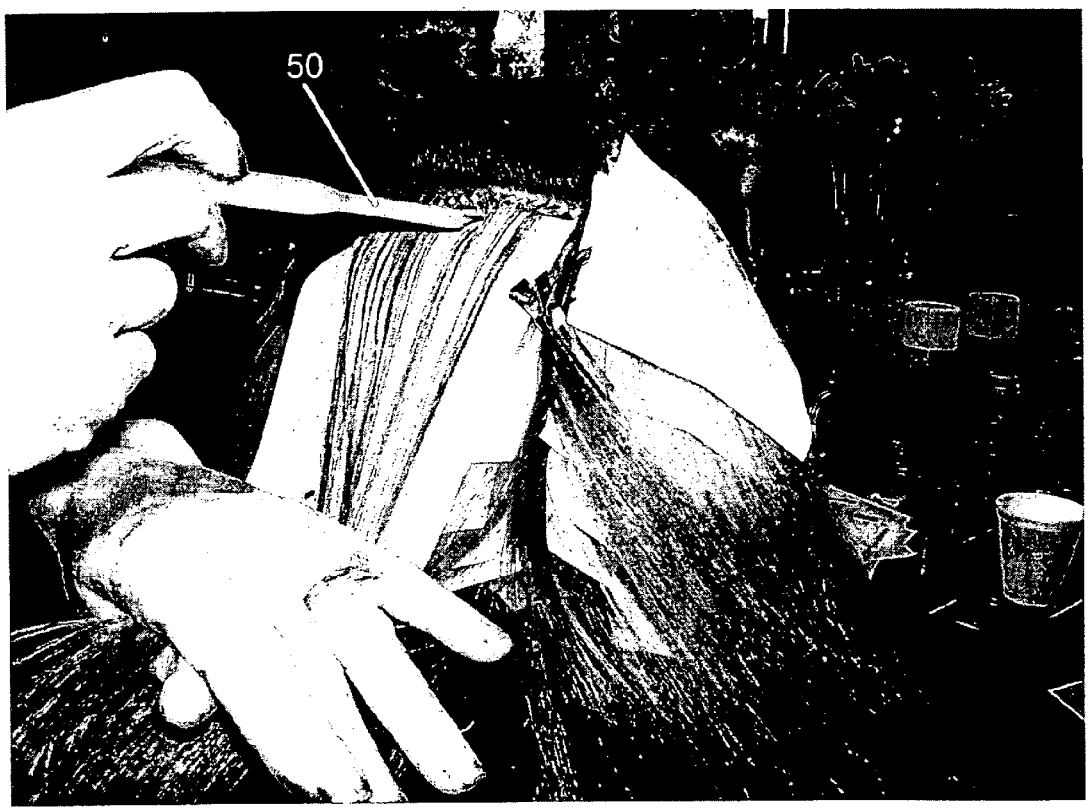
FIG. 9 depicts the painting of the coloring onto the hair strands using a brush.
Figure 10:
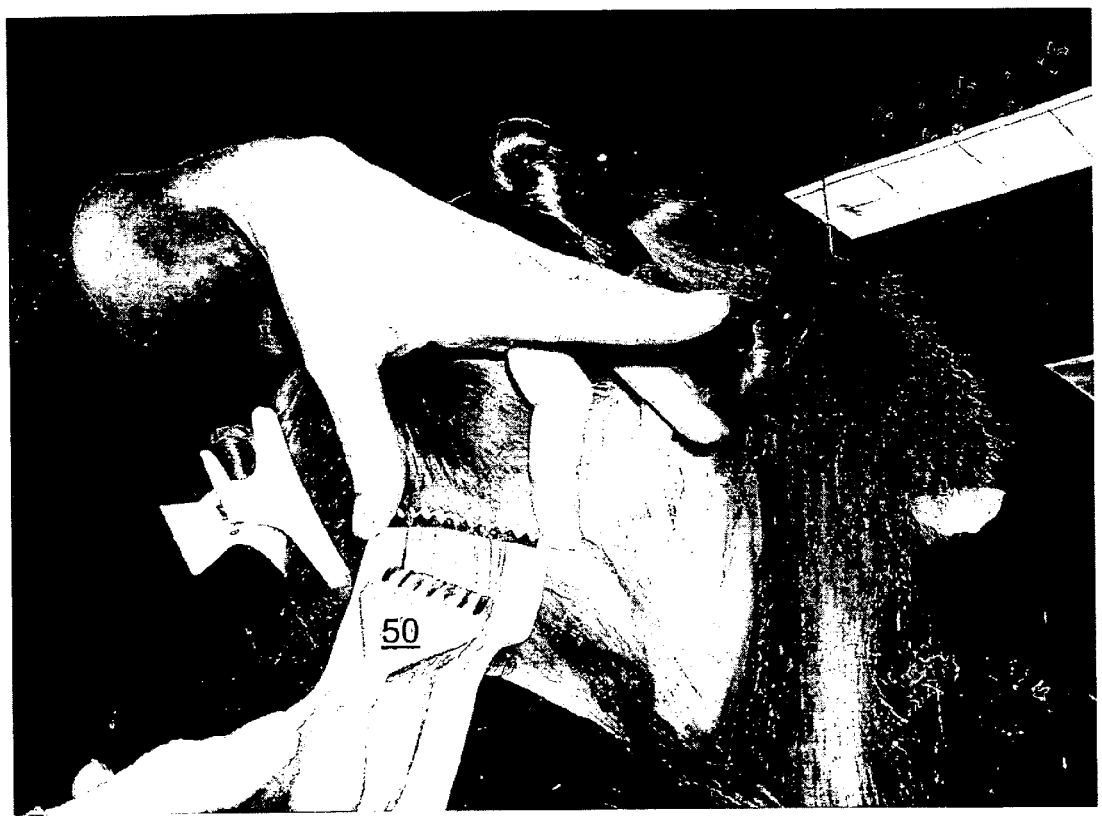
FIG. 10 depicts another view of the process of FIG. 9.

Referring now to FIGS. 9 and 10, a liquid chemical hair color mixture is applied to the hair on the foil by means of a brush or sponge, being careful not to let the mixture contact any surrounding hair. The hair can be worked on the foil to insure a proper coating of the coloring chemicals. In this embodiment the coloring chemicals are provided separately from the foil, and are not a part of this invention.

Figure 11:
FIG. 11 depicts the folding of the foil with the hair strands within.

Referring now to FIG. 11, the foil is folded in half lengthwise, bringing the bottom edge 40 in alignment with the top edge 32, and creating a pocket for the hair to absorb and react to the coloring chemicals. The liquid chemical mixture also acts as an adhesive to maintain the foil in its folded position.

Figure 12:
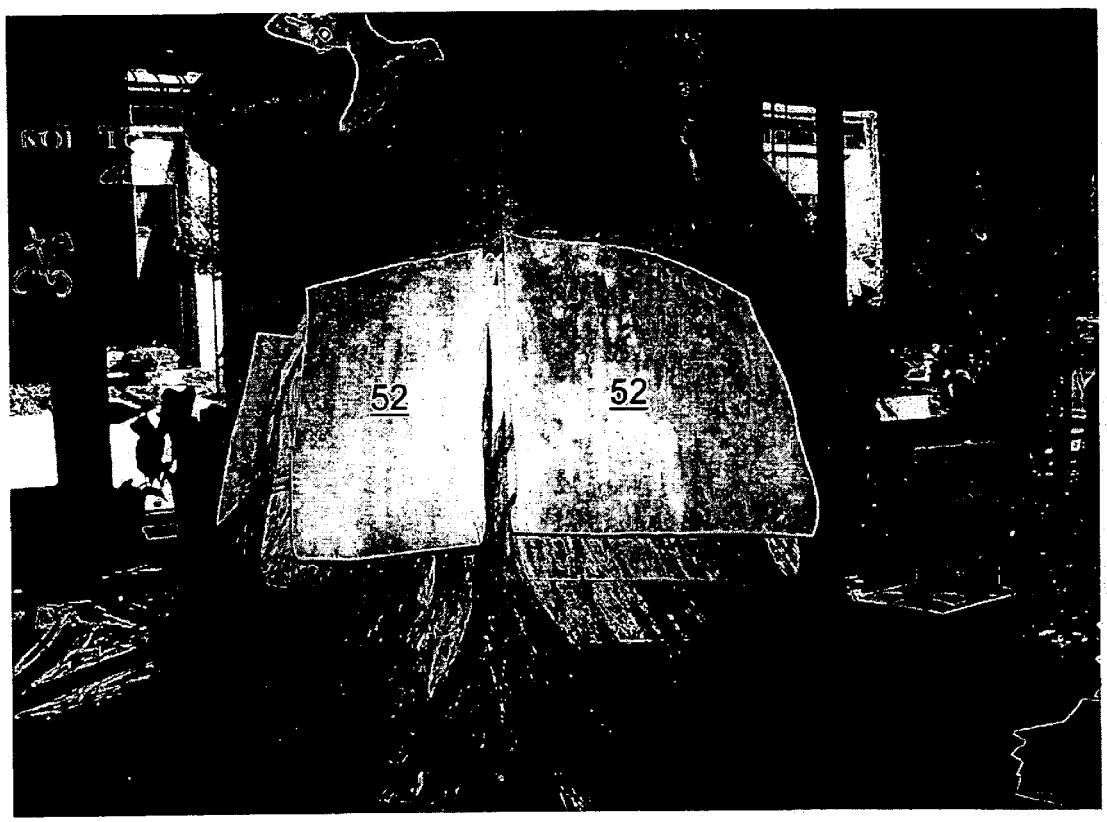
FIG. 12 depicts the subject's head with all of the foils attached.

When all of the foils have been attached to the head of the subject, the coloring chemicals applied, and the foils folded 52, the head of the subject appears as shown in FIG. 12. In this figure, the process recited above has been repeated until the entire region of the head to be colored has been covered with folded foils.

Finally, depending on the chemical mixture used, a different processing time for the coloring chemical to work is required. The stylist may simply wait a certain time, based on experience, for the coloring to work to the degree required. Alternatively, the curing process may be accelerated by the application of heat. Heat from a hair dryer or heat lamp may be used in this regard.

The embodiment of the foil as seen in FIGS. 4a and 4b is intended for home use, and the method using said embodiment is slightly different from that described above. The steps of FIGS. 9 and 10 may also be followed using the foil of FIGS. 4a and 4b. However, since the coloring chemicals are contained entirely within the foam pad 48, the user does not need to purchase coloring supplies separately from the foils. Instead, the user moistens the foam pad with a brush to a workable consistency, and then paints the coloring chemicals onto the hair strands using the same brush. In some embodiments, the foam pad contains already moistened mixtures of bleach or color, sealed with a peel-off film, so that moistening is not necessary. Furthermore, the foam pad, although primarily intended for home use, may also be attractive for use in commercial environments.

When the hair strands have been sufficiently saturated with the coloring the foil is folded as before. The foam pad does not prevent the folded foil from remaining folded and in place, and attached to the hair strands within.

While the invention has been described with reference to specific embodiments, it will be apparent that improvements and modifications may be made within the purview of the invention without departing from the scope of the invention defined in the appended claims.

I claim:

1. A foil comprising a sheet of rectangular material with a pinked top edge, and an attachment anchor configured on one surface of said sheet proximate the pinked top edge, said attachment anchor comprising an elongate, substantially linear section of hook fastener material having a long axis substantially parallel to the pinked top edge of the foil, and a pinked edge in close proximity to the pinked top edge of said foil.

2. The foil of claim 1, wherein the attachment anchor is substantially rectangular.

3. A foil according to claim 1, said foil having defined upper and lower surfaces, said attachment anchor being configured on the lower surface, the upper surface of the foil being configured with a hair positioning restraint consisting of a section of hair-adherent material.

4. The foil of claim 3, wherein the long axis of the hair positioning restraint is disposed about one-quarter inch from the top edge of the foil.

5. The foil of claim 3, wherein the hair positioning restraint comprises hook fastener material.

6. The foil of claim 3, wherein the hair positioning restraint is substantially rectangular.

7. The foil of claim 1, said foil comprising upper and lower surfaces, said attachment anchor being attached to said lower surface, wherein the lower surface of the sheet comprises a moisture barrier, and the upper surface further comprises a slightly moisture absorbent material.

8. The foil of claim 1, wherein the sheet is transparent.

9. A foil according to claim 1, comprising means to reinforce the pinked top edge.

10. A foil according to claim 1, further comprising a foam pad attached to the surface opposite said attachment anchor proximate the pinked top edge, said foam pad containing coloring agents.

11. A foil according to claim 10, said foam pad extending the width of the foil.

12. A method of coloring hair comprising the steps:
dividing the hair on a subject's head into workable segments separated by parts;
using a foil comprising a sheet of rectangular material with upper and lower surfaces and a pinked top edge, an attachment anchor configured on the lower surface of said sheet proximate the top edge, said attachment anchor comprising an elongated, substantially linear section of hook fastener material having a long axis substantially parallel to the pinked top edge, and a hair positioning restraint configured on the upper surface of said sheet:
attaching the lower surface of the foil to the subject's scalp with the pinked top edge just below a selected said part such that the anchor attachment holds the foil in place;
drawing strands of hair from under the foil through the attachment anchor; pressing the strands of hair over the pinked top edge and down against the hair positioning restraint;
realigning the hair positioning restraint in its original position;
applying a hair color mixture to the strands of hair on the foil; and
folding the foil in half lengthwise, bringing the bottom edge in alignment with top edge.

13. A method of coloring hair comprising the steps:
dividing the hair on a subject's head into workable segments separated by parts;
using a foil comprising a sheet of rectangular material with a pinked top edge and configured with an attachment anchor on one surface of the sheet proximate the top edge, said attachment anchor comprising an elongated, substantially linear section of hook fastener material having a long axis substantially parallel to the pinked top edge of the foil, and a pinked edge in close proximity to the pinked top edge of said foil;
attaching the foil to the subject's scalp with the pinked top edge just below a selected said part such that the anchor attachment holds the foil in place;
drawing selected strands of hair from under the foil through the attachment anchor;
laying the strands of hair across the pinked top edge and onto the exposed surface of the foil;
applying a hair color mixture to the strands of hair on the foil; and
folding the foil in half lengthwise, bringing the bottom edge in alignment with top edge.

* * * * *